(12) United States Patent
Ito

(10) Patent No.: US 8,419,625 B2
(45) Date of Patent: Apr. 16, 2013

(54) ENDOSCOPE APPARATUS FOR CLEANING TRANSPARENT MEMBER

(75) Inventor: Hiroshi Ito, Hachioji (JP)

(73) Assignee: Olympus Corporation, Tokyo (JP)

( * ) Notice: Subject to any disclaimer, the term of this patent is extended or adjusted under 35 U.S.C. 154(b) by 153 days.

(21) Appl. No.: 13/156,694

(22) Filed: Jun. 9, 2011

(65) Prior Publication Data
US 2011/0313253 A1 Dec. 22, 2011

(30) Foreign Application Priority Data
Jun. 18, 2010 (JP) .................................. 2010-139617

(51) Int. Cl.
*A61B 1/00* (2006.01)
*A61B 1/015* (2006.01)

(52) U.S. Cl.
USPC .......................................... 600/157; 600/176

(58) Field of Classification Search .................. 600/157, 600/129, 176, 169
See application file for complete search history.

(56) References Cited

U.S. PATENT DOCUMENTS

| | | | | |
|---|---|---|---|---|
| 4,870,950 A * | 10/1989 | Kanbara et al. | ............... | 600/109 |
| 6,091,406 A * | 7/2000 | Kambara et al. | ............... | 345/177 |
| 7,896,804 B2 * | 3/2011 | Uchimura et al. | ............ | 600/173 |
| 8,303,492 B2 * | 11/2012 | Ito | ................................. | 600/176 |
| 2005/0243071 A1 * | 11/2005 | Kent et al. | ..................... | 345/177 |
| 2008/0188714 A1 * | 8/2008 | McCaffrey | ..................... | 600/157 |
| 2008/0319266 A1 * | 12/2008 | Poll et al. | ...................... | 600/157 |
| 2009/0264701 A1 | 10/2009 | Ito | | |
| 2010/0219047 A1 * | 9/2010 | Xu et al. | ....................... | 198/617 |

FOREIGN PATENT DOCUMENTS

| | | |
|---|---|---|
| EP | 2 110 070 A1 | 10/2009 |
| JP | 2006-55275 A | 3/2006 |
| JP | 2009-254571 | 11/2009 |

OTHER PUBLICATIONS

Humphryes, R.F., et al. "Acoustic Bulk-Surface-Wave Transducer", Electronic Letters, Jan. 1, 1969, vol. 5, No. 9, p. 175.
Extended European Search Report dated Sep. 30, 2011 from corresponding European Patent Application No. 11 16 9935.1.

* cited by examiner

*Primary Examiner* — John P Leubecker
(74) *Attorney, Agent, or Firm* — Scully Scott Murphy & Presser, PC

(57) ABSTRACT

An endoscope apparatus includes a transparent member provided at a distal end of an insertion portion of an endoscope, opposed to an image pickup optical system, a transducer attached to an inner surface of the transparent member, a diffraction grating provided on an outer surface of the transparent member, for converting ultrasound vibration from the transducer to a surface acoustic wave Φ that propagates on the outer surface of the transparent member and a conversion section provided in an outer peripheral corner of the transparent member for converting the surface acoustic wave Φ to a bulk wave Φb that scatters into the transparent member.

8 Claims, 9 Drawing Sheets

ENDOSCOPE APPARATUS FOR CLEANING TRANSPARENT MEMBER

CROSS REFERENCE TO RELATED APPLICATION

This application claims benefit of Japanese Application No. 2010-139617 filed in Japan on Jun. 18, 2010, the contents of which are incorporated by this reference.

BACKGROUND OF THE INVENTION

1. Field of the Invention

The present invention relates to an endoscope apparatus that reliably removes adherent substances from a surface of an observation window and thereby improves observability.

2. Description of the Related Art

In recent years, surgery using an endoscope aiming at minimally invasive medical treatment is becoming increasingly common. A challenge to such surgery under endoscopy is how to prevent deterioration of an observation environment due to adhesion of dirt to or fogging on an observation window disposed at a distal end portion of the endoscope.

Endoscopes for digestive organs remove fogging and dirt by supplying water to a lens at the distal end portion of the endoscope. In the case of transnasal endoscopes in particular, there may be cases where water droplets are not effectively removed after a water supply or air supply. Furthermore, in the case of endoscopes for surgery, there may be cases where adhered dirt consists of scattered blood, fat or the like resulting from surgery, which cannot be removed simply by supplying water.

As a solution for this problem, for example, a technique disclosed in Japanese Patent Application Laid-Open Publication No. 2009-254571 is known.

This conventional endoscope apparatus is provided with a transparent member provided opposed to an image pickup optical system at the distal end of an insertion portion, a transducer attached to the inner surface of the transparent member and a diffraction grating provided on the outer surface of the transparent member for converting ultrasound vibration from the transducer to a surface acoustic wave that propagates on the outer surface of the transparent member. The transducer attached to the inner surface of the transparent member and the diffraction grating on the outer surface of the transparent member are provided in the vicinity of the outer circumference of the transparent member so as not to block the field of view of the image pickup optical system.

Ultrasound vibration radiated from the transducer is converted to a surface acoustic wave by the diffraction grating on the outer surface of the transparent member and radiated in the direction of a grating vector of the diffraction grating. Here, the grating vector of the diffraction grating is defined as a direction of periodicity of the diffraction grating. The surface acoustic wave radiated from the diffraction grating propagates from the vicinity of the outer circumference of the transparent member in the direction of the observation field of view of the image pickup optical system in the center of the transparent member, acts on the water or dirt that blocks the visibility within the observation field of view and removes the water or dirt from the observation field of view.

SUMMARY OF THE INVENTION

An endoscope apparatus according to an aspect of the present invention includes a transparent member provided at a distal end of an insertion portion of an endoscope, opposed to an image pickup optical system, a transducer attached to an inner surface of the transparent member, a diffraction grating provided on an outer surface of the transparent member to convert ultrasound vibration from the transducer to a surface acoustic wave that propagates on the outer surface of the transparent member, and a conversion section that converts the surface acoustic wave to a bulk wave that scatters into the transparent member in an outer peripheral corner of the transparent member.

The above and other objects, features and advantages of the invention will become more clearly understood from the following description referring to the accompanying drawings.

DETAILED DESCRIPTION OF THE PREFERRED EMBODIMENTS

Hereinafter, an endoscope apparatus which is the present invention will be described. In the following descriptions, it should be noted that drawings based on respective embodiments are schematic ones and the relationship between the thickness and width of each part, a thickness ratio among the respective parts or the like are different from the actual ones, and parts whose relationship and ratios in size are also different among the drawings may be included.

First Embodiment

A first embodiment of the present invention will be described based on the accompanying drawings first. In the following descriptions, a rigid endoscope for performing a laparoscopic surgical operation will be illustrated as an example.

Figure 1:
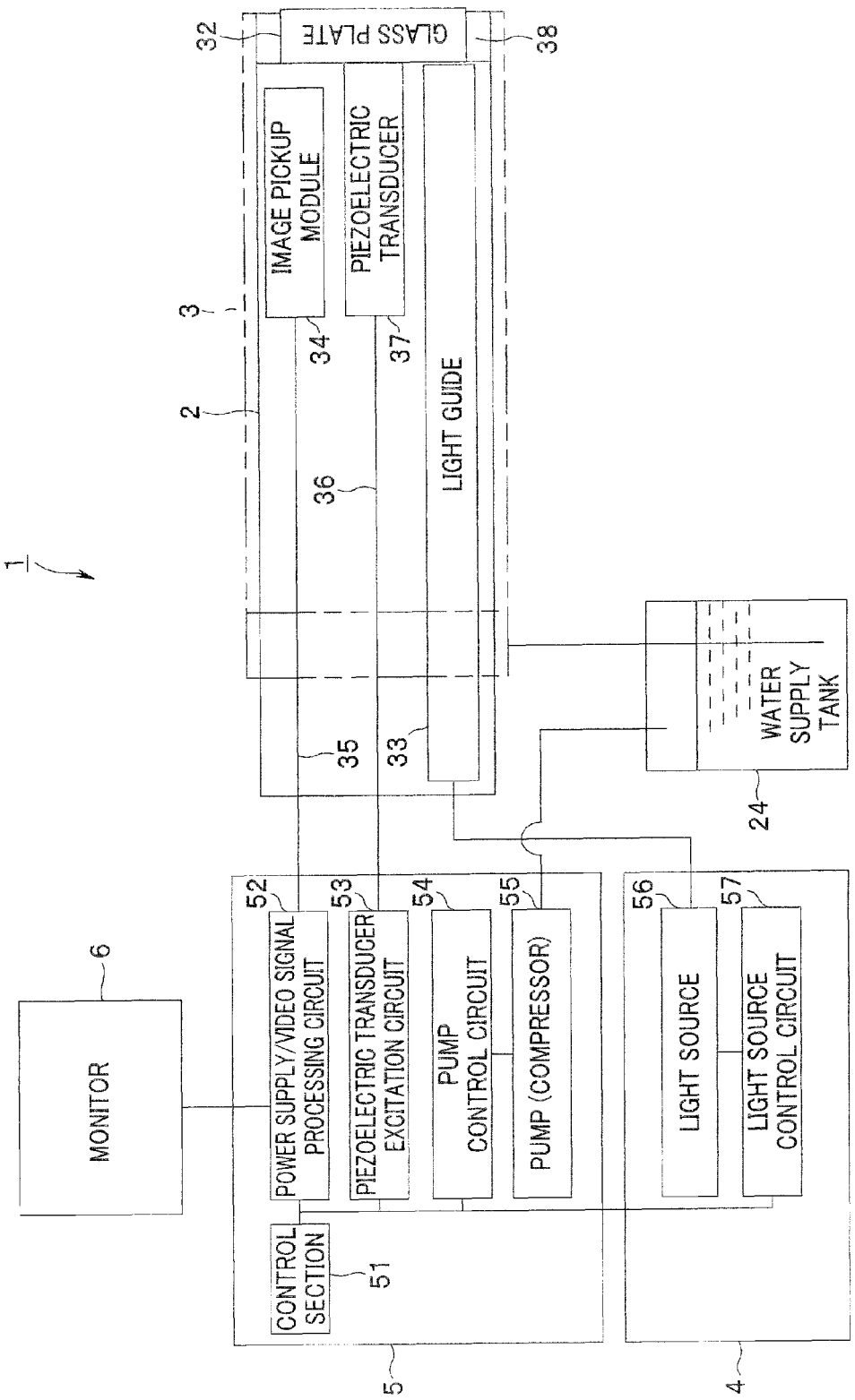
FIG. 1 is a block diagram mainly illustrating an overall configuration and an electric configuration of an endoscope system according to a first embodiment of the present invention.
Figure 2B:
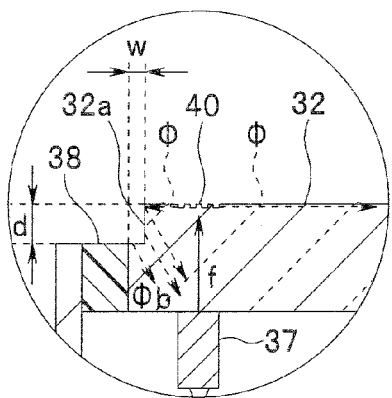
FIG. 2B is an enlarged cross-sectional view of a circled portion in FIG. 2A according to the first embodiment of the present invention.
Figure 2A:
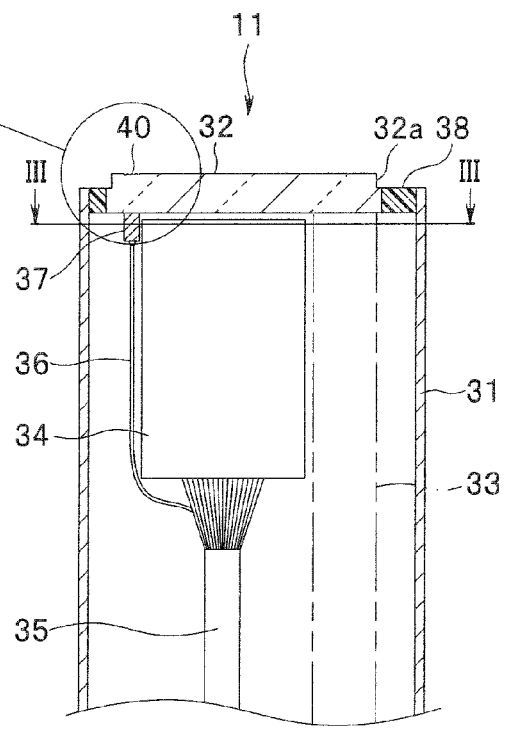
FIG. 2A is a cross-sectional view illustrating a configuration of the distal end portion of a rigid endoscope according to the first embodiment of the present invention.
Figure 3:
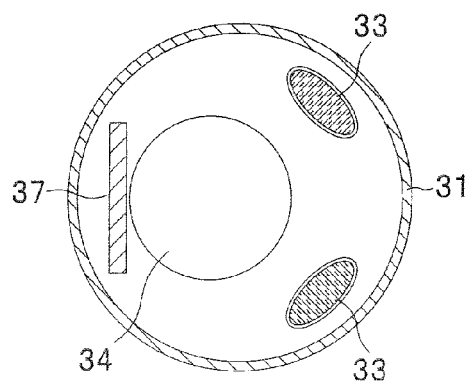
FIG. 3 is a cross-sectional view of the distal end portion cut along a line III-III in FIG. 2A according to the first embodiment of the present invention.
Figure 4:
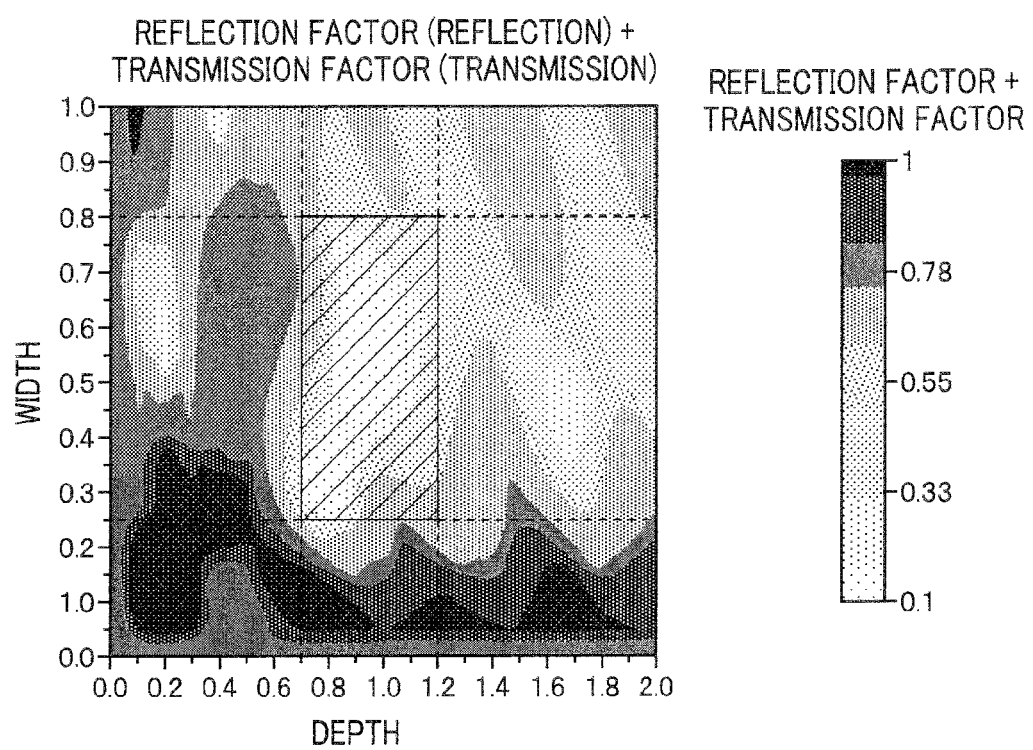
FIG. 4 is a graph verifying a relationship between a depth and a width of a stepped portion that deflects a surface acoustic wave and converts the surface acoustic wave to a bulk wave scattering into a glass plate according to the first embodiment of the present invention.
Figure 5:
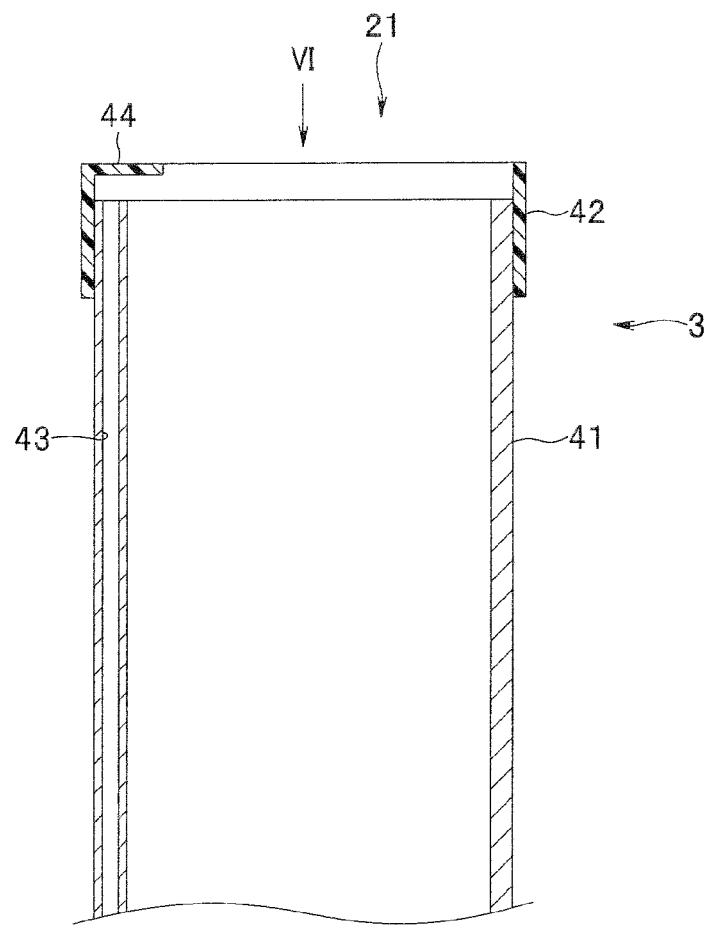
FIG. 5 is a cross-sectional view illustrating a configuration of the distal end portion of a water supply sheath according to the first embodiment of the present invention.
Figure 6:
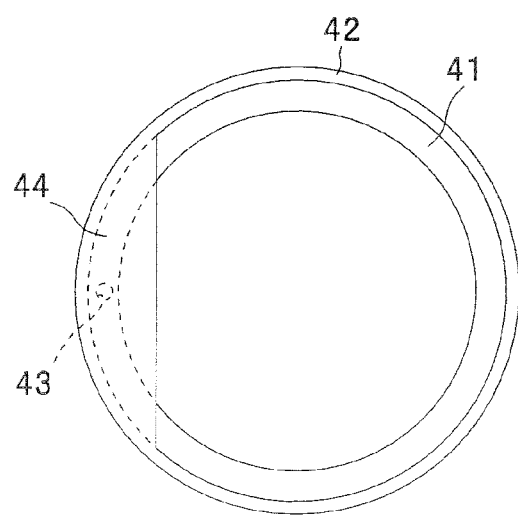
FIG. 6 is a plan view illustrating a configuration of the water supply sheath viewed in the direction of an arrow VI in FIG. 5 according to the first embodiment of the present invention.
Figure 7:
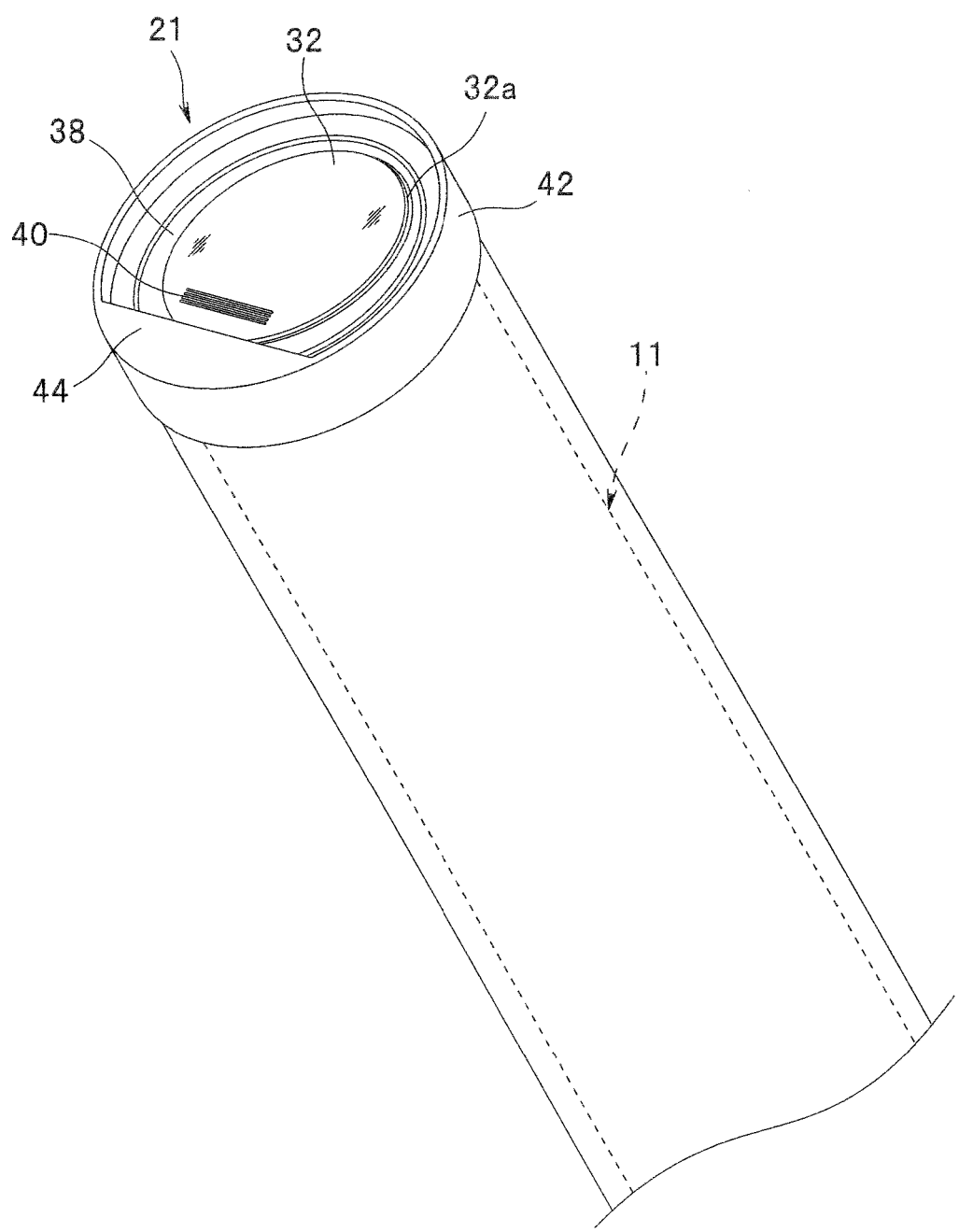
FIG. 7 is a perspective view of the distal end portion illustrating the insertion portion of the rigid endoscope inserted in the water supply sheath according to the first embodiment of the present invention.
Figure 8:
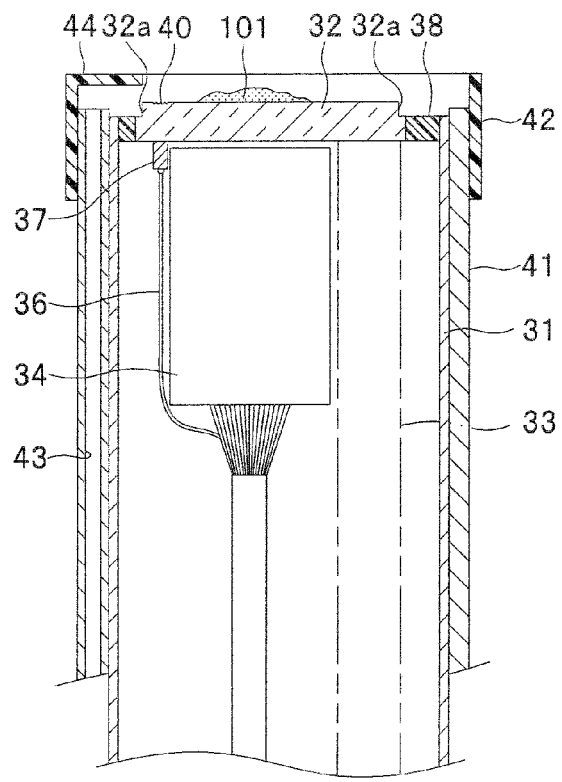
FIG. 8 is a cross-sectional view of the distal end portion illustrating the insertion portion of the rigid endoscope inserted in the water supply sheath and illustrating an adherent substance stuck to the observation window according to the first embodiment of the present invention.
Figure 9:
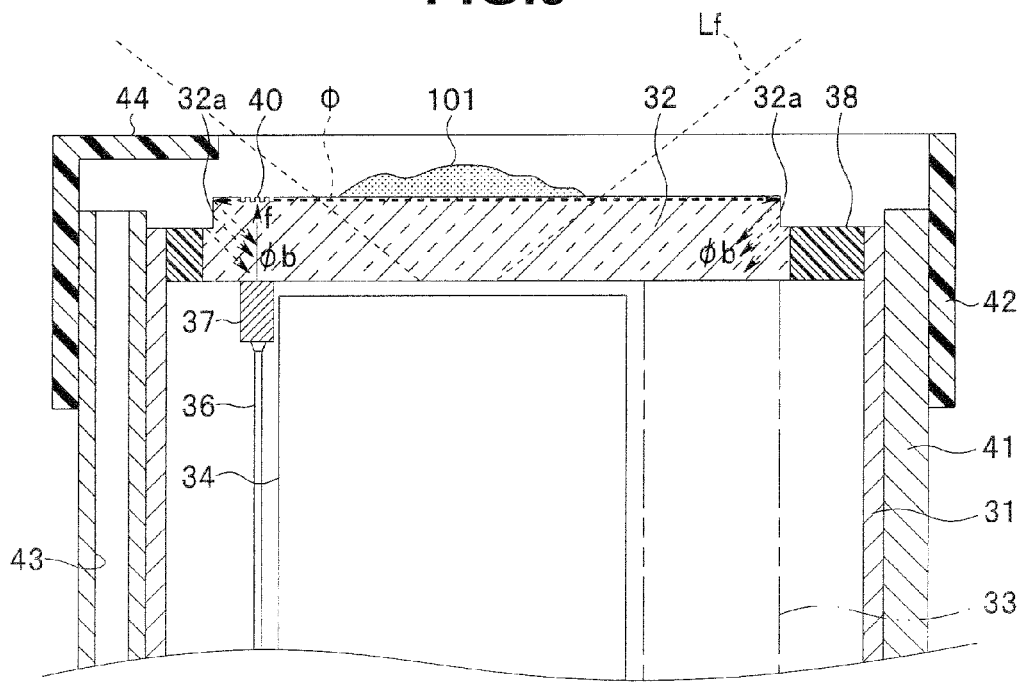
FIG. 9 is an enlarged view of the distal end portion illustrating the insertion portion of the rigid endoscope in FIG. 8 inserted into the water supply sheath according to the first embodiment of the present invention.
Figure 10:
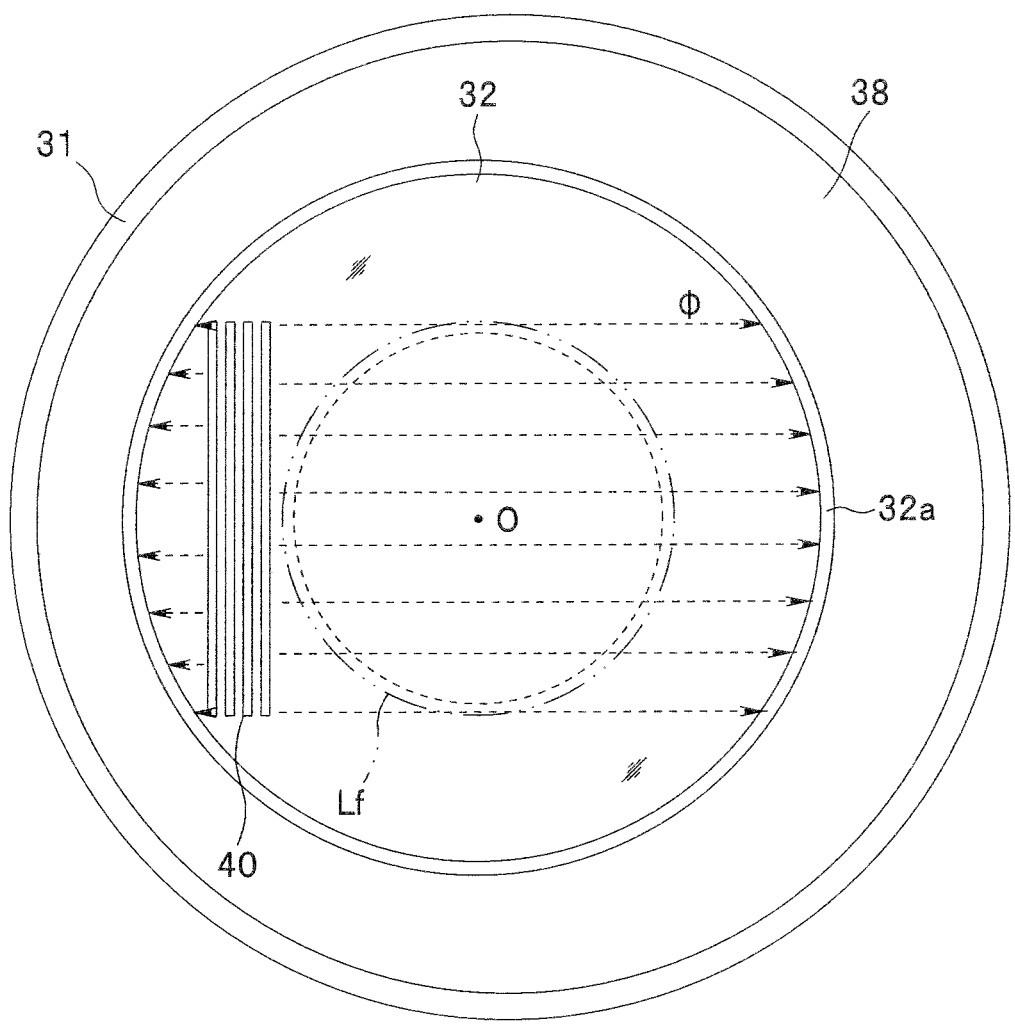
FIG. 10 is a plan view illustrating a front end face of the rigid endoscope to illustrate propagation of the surface acoustic wave according to the first embodiment of the present invention.

Furthermore, FIG. 1 to FIG. 10 are related to the first embodiment of the present invention, FIG. 1 is a block diagram mainly illustrating an overall configuration and an electric configuration of an endoscope system, FIG. 2A is a cross-sectional view illustrating a configuration of the distal end portion of a rigid endoscope, FIG. 2B is an enlarged cross-sectional view of a circled portion in FIG. 2A, FIG. 3 is a cross-sectional view of the distal end portion cut along a line III-III in FIG. 2A, FIG. 4 is a graph verifying a relationship between a depth and a width of a stepped portion that deflects a surface acoustic wave and converts the surface acoustic wave to a bulk wave scattering into a glass plate, FIG. 5 is a cross-sectional view illustrating a configuration of the distal end portion of a water supply sheath, FIG. 6 is a plan view illustrating a configuration of the water supply sheath viewed in the direction of an arrow VI in FIG. 5, FIG. 7 is a perspective view of the distal end portion illustrating the insertion portion of the rigid endoscope inserted in the water supply sheath, FIG. 8 is a cross-sectional view of the distal end portion illustrating the insertion portion of the rigid endoscope inserted in the water supply sheath and illustrating an adherent substance stuck to the observation window, FIG. 9 is an enlarged view of the distal end portion illustrating the insertion portion of the rigid endoscope inserted in the water supply sheath in FIG. 8 and FIG. 10 is a plan view illustrating a front end face of the rigid endoscope to illustrate propagation of the surface acoustic wave.

As shown in FIG. 1, an endoscope system 1 which is an endoscope apparatus of the present embodiment is mainly constructed of a rigid endoscope (hereinafter simply referred to as "endoscope") 2, a water supply sheath 3 constituting cleaning liquid supply means into which an insertion portion 11 of the endoscope 2 is inserted and arranged, a video processor 5, a light source device 4 and a monitor 6.

Since the endoscope 2 has a configuration similar to a conventional one, none of the components thereof is shown but the endoscope 2 is configured by including an operation section provided linked to the rigid insertion portion 11 (see FIG. 2), switches provided in the operation section, a universal cable which is a composite cable that extends from the operation section, a light source connector disposed at an extending end of the universal cable, an electric cable that extends from a side of the light source connector, and an electric connector disposed at an extending end of the electric cable. The light source connector is detachably connected to the light source device 4. Furthermore, the electric connector is detachably connected to the video processor 5.

Furthermore, the video processor 5 is electrically connected to the light source device 4 and the monitor 6. The video processor 5 transforms image data picked up by the endoscope 2 into a video signal and causes the monitor 6 to display the video signal. The video processor 5 constitutes a control apparatus which is control means for receiving operation signals of the switches disposed in the operation section of the endoscope 2 as input, controlling the light source device 4 based on these signals, sending air to a water supply tank 24 and controlling the supply of a physiological salt solution which is cleaning water in the water supply tank 24 to the water supply sheath 3 or the like.

Next, the main electric configuration of the endoscope system 1 will be described below based on FIG. 1.

As shown in FIG. 1, the video processor 5 is configured by including a control section 51 which is a CPU, a power supply/video signal processing circuit 52, a piezoelectric transducer excitation circuit 53, a pump control circuit 54 and a pump 55 which is a compressor.

The control section 51 is electrically connected to the power supply/video signal processing circuit 52, the piezoelectric transducer excitation circuit 53 and the pump control circuit 54, and controls the respective circuits. Furthermore, the power supply/video signal processing circuit 52 is also electrically connected to the monitor 6 and outputs an endoscope image signal to the monitor 6.

The piezoelectric transducer excitation circuit 53 has a function of causing the piezoelectric transducer 37 of the endoscope 2 to oscillate and controls vibration intensity of the piezoelectric transducer 37 so as to change according to the amount of power outputted under the control of the control section 51.

The pump control circuit 54 is electrically connected to the pump 55 and outputs an electric signal for drive-controlling the pump 55 under the control of the control section 51.

The light source device 4 is configured by including a light source 56 such as halogen lamp and a light source control circuit 57 that drives the light source 56. The light source control circuit 57 is electrically connected to the control section 51 of the video processor 5 and is controlled by the control section 51.

Next, the configuration of the distal end portion of the insertion portion 11 of the endoscope 2 will be described based on FIG. 2 and FIG. 3 below.

As shown in FIGS. 2A and 2B and FIG. 3, in the insertion portion 11 of the endoscope 2, a fixed support member 38 is engaged with and fixed to the distal end of a metallic tubular member 31 that constitutes an insertion portion outer sheath. A transparent quasi-disk-shaped glass plate 32 which is an observation window supported and fixed so that the perimeter thereof is covered with the fixed support member 38 is bonded by means of solder, adhesive or the like.

An image pickup module 34 including an image pickup optical system and two illumination light guides 33 are set up inside the tubular member 31. Though not shown in detail, an image forming optical system, a solid image pickup device and a driver chip thereof constituting the image pickup optical system are incorporated in the image pickup module 34 and a communication cable 35 is drawn toward its root.

Furthermore, a rectangular piezoelectric transducer 37 is attached at a position not blocking the observation field of view on the inner surface (back) of the glass plate 32, that is, on one region side outside the image pickup module 34 arranged on the opposite side (here, in a direction at a predetermined distance from part of the outer circumference). A wiring 36 is connected to the piezoelectric transducer 37 so that the piezoelectric transducer 37 is electrically driven. That is, the wiring 36 to supply a voltage for excitation is drawn from the piezoelectric transducer 37 toward the root of the endoscope 2. Furthermore, the fixing of the piezoelectric transducer 37 to the glass plate 32 is not limited to the fixing by means of an adhesive, but may also be fixing by solder or the like. By being driven at a resonance frequency or in the vicinity of the resonance frequency, the piezoelectric transducer 37 generates ultrasound vibration in the glass plate 32.

The glass plate 32 is provided with a diffraction grating 40 having a rectangular cross section with a plurality of linear grooves formed in parallel at a position on the outer surface facing the piezoelectric transducer 37 attached to the inner surface (back) as shown in FIG. 2B. That is, the area of the portion of the piezoelectric transducer 37 attached to the inner surface of the glass plate 32 is equal to or greater than the area of the diffraction grating 40 formed on the outer surface of the glass plate 32.

Ultrasound vibration f generated from the above described piezoelectric transducer 37 (see FIG. 9 and FIG. 10) mainly propagates in a direction perpendicular to the surface of attachment of the piezoelectric transducer 37 (inner surface of the glass plate 32) and impinges on the diffraction grating 40 of the glass plate 32 facing the piezoelectric transducer 37. The ultrasound vibration that enters the diffraction grating 40 is converted to a surface acoustic wave $\Phi$ (see FIG. 9, FIG. 10) that propagates on the outer surface of the glass plate 32 by the diffraction grating 40.

According to the present embodiment, the grating period which is a structure parameter of the diffraction grating 40 is a value obtained by dividing the speed of surface acoustic wave $\Phi$ that propagates through the glass plate 32 by the frequency of the ultrasound vibration f and is a value substantially the same as the wavelength of the surface acoustic wave $\Phi$ radiated from the diffraction grating 40. Furthermore, the depth of the grooves of the diffraction grating 40 is set to approximately 1/10 of the grating period.

Furthermore, the components of the endoscope 2 are sealed by the tubular member 31 and the glass plate 32 bonded thereto, providing a structure resistant to sterilization processing with high pressure vapor.

Furthermore, although the present embodiment assumes the inner surface facing the image pickup optical system of the image pickup module 34 of the glass plate 32 to be planar, part of the surface facing the image pickup optical system may be convex or concave to form a part of the image pickup optical system.

Furthermore, the light guide 33 of the present embodiment extends to the universal cable and the light guide 33 is terminated at the light source connector. The communication cable 35 and the wiring 36 are connected to the electric connector via an electric cable.

That is, via the universal cable and the electric cable, the endoscope 2 has such a configuration that the light guide 33 is connected to the light source 56 of the light source device 4 including the light source control circuit 57, the communication cable 35 drawn from the image pickup module 34 is connected to the power supply/video signal processing circuit 52 of the video processor 5 and the wiring 36 drawn from the piezoelectric transducer 37 is connected to the piezoelectric transducer excitation circuit 53 constituting the excitation means of the video processor 5.

As shown in FIG. 2, a stepped portion 32a having a stepped structure is formed in the corners where the surface constituting the outer surface of the glass plate 32 of the present embodiment and the side periphery surface (side surface) constituting the outer circumferential face intersect each other. The depth d and width w of the stepped portion 32a are set according to a reflection factor (reflection) and a transmission factor (transmission). The reflection factor is a ratio of a reflected (surface acoustic) wave, which is reflected from the stepped portion 32 and propagates in an opposite direction of an incident (surface acoustic) wave, to the incident (surface acoustic) wave, which propagates into the stepped portion 32a. The transmission factor is a ratio of a transmitted (surface acoustic) wave, which propagates on the side periphery surface (side surface), to the incident wave. A bulk wave $\Phi b$ is an elastic wave which is a scattering of the surface acoustic wave $\Phi$ incident upon the stepped portion 32a and propagates into the inside of the glass plate 32.

To be more specific, the stepped portion 32a is formed in the corners where the surface and the side periphery surface (side surface) of the glass plate 32 intersect each other, which falls within a predetermined range of numerical values of the depth d (d=$0.7\lambda$ to $1.2\lambda$) and width w (w=$0.25\lambda$ to $0.8\lambda$) relative to the wavelength $\lambda$ of the surface acoustic wave $\Phi$. The wavelength $\lambda$ of the surface acoustic wave $\Phi$ is a value obtained by dividing the velocity of sound of the surface acoustic wave $\Phi$ determined from the physical property values of the glass plate 32 by the frequency of ultrasound generated by the piezoelectric transducer 37.

In the relationship between the depth d and width w of the stepped portion 32a, as shown in FIG. 4, a verification result is obtained which shows that the bulk wave $\Phi b$ that scatters into the glass plate 32 becomes smaller as the sum of the reflection factor (reflection) and the transmission factor (transmission) approximates to 1.0, that is, the concentration becomes higher, whereas the bulk wave $\Phi b$ that scatters into the glass plate 32 becomes greater as the sum of the reflection factor and the transmission factor approximates to 0, that is, the concentration becomes lower. That is, as the sum of the reflection factor and the transmission factor decreases, the surface acoustic wave $\Phi$ is converted to the bulk wave $\Phi b$ that scatters into the glass plate 32 by the stepped portion 32a.

For this reason, as shown in FIG. 4, a verification result is obtained which shows that when the stepped portion 32a converts most of the incident surface acoustic wave $\Phi$ of wavelength $\lambda$ to the bulk wave $\Phi b$, causing the surface acoustic wave to scatter into the glass plate 32, the depth d and the width w fall within a range of numerical values of depth d=$0.7\lambda$ to $1.2\lambda$ and width w=$0.25\lambda$ to $0.8\lambda$.

As for the width w of the stepped portion 32a, the size in the direction in which the surface acoustic wave $\Phi$ propagates, that is, the size in the direction parallel to the direction of propagation of the surface acoustic wave $\Phi$ within the outer surface (within the surface) of the glass plate 32 is defined. Furthermore, as for the depth d of the stepped portion 32a, the size in a direction perpendicular to the direction of propagation of the surface acoustic wave $\Phi$ within the outer surface of the glass plate 32, that is, the size in the direction orthogonal to the outer surface (surface) of the glass plate 32 is defined.

Thus, the stepped portion 32a of the present embodiment, defined by numerical values within the above described range the depth d (d=$0.7\lambda$ to $1.2\lambda$) and the width w (w=$0.25\lambda$ to $0.8\lambda$), acts as a mode conversion section that converts the incident surface acoustic wave $\Phi$ to the bulk wave $\Phi b$ so as to scatter into the glass plate 32 which is a transparent member. That is, since it is preferable to set the depth d and the width w of the stepped portion 32a such that both the reflection factor (reflection) and transmission factor (transmission) are small and the bulk wave $\Phi b$ that scatters into the glass plate 32 increases, the present embodiment sets the depth d and the width w within the above described range of numerical values (d=$0.7\lambda$ to $1.2\lambda$, w=$0.25\lambda$ to $0.8\lambda$).

To prevent deterioration in the productivity, the aforementioned stepped portion 32a is formed in the corners of the entire circumference of the glass plate 32, but the stepped portion 32a may be naturally formed only in the outer circumference corner region of the glass plate to which the surface acoustic wave Φ, which is converted from ultrasound vibration generated by the piezoelectric transducer 37 at the diffraction grating 40, reaches.

Next, the water supply sheath 3 will be described below based on FIG. 5 and FIG. 6.

The water supply sheath 3 is configured by including a coated tube 21 provided with a distal end member, a connection section (not shown) provided linked to the proximal end of the coated tube 21 and a water supply tube (not shown) that extends from a side of the connection section. The extending end of the water supply tube is connected to the water supply tank 24. One end of an air supply tube (not shown) is connected to an air supply connector of the video processor 5 and the other end is connected to the water supply tank 24.

The coated tube 21 of the water supply sheath 3 is configured by including a tube main body 41 and a quasi-cylindrical distal end member 42 engaged with the distal end of the tube main body 41. One water supply channel 43 for water supply having a circular cross section is formed in part of the thick portion of the tube main body 41. The water supply channel 43 extends to the connection section and communicates with the water supply tube via the connection section.

The distal end member 42 has a flanged portion 44 which is a plate body disposed along the end face of the opening at a position facing the water supply channel 43 of the tube main body 41.

The water supply sheath 3 configured in this way is connected so that the water supply channel 43 communicates with the water supply tank 24 via the water supply tube. When the pressure in the water supply tank 24 is increased by the air from the pump 55 controlled by the pump control circuit 54, a physiological salt solution or the like which is cleaning water in the water supply tank 24 is supplied into the water supply channel 43 and flows into the distal end portion of the endoscope.

In the endoscope system 1 of the present embodiment described above, the insertion portion 11 of the endoscope 2 is inserted into the coated tube 21 of the water supply sheath 3 as shown in FIG. 7, and is used, for example, for a laparoscopic surgical operation.

In the endoscope system 1, when dirt 101 such as blood or fat is stuck to the outer surface of the glass plate 32 during an operation as shown in FIG. 8, the user who is a medical doctor operates remote switches of the switches provided in the operation section of the endoscope 2. An excitation signal is then supplied to the piezoelectric transducer 37 from the piezoelectric transducer excitation circuit 53 of the video processor 5 according to a control signal through this switch operation and ultrasound vibration f is generated in the glass plate 32.

Prior to this, cleaning water is supplied to the outer surface of the glass plate 32 from the water supply sheath 3 through the operation of the above described switches. That is, air is supplied into the water supply tank 24 from the pump 55 which is a compressor and cleaning water in the water supply tank 24 is supplied to the water supply sheath 3. The cleaning water jets out from the distal end of the tube main body 41 via the water supply channel 43 formed in the tube main body 41 of the water supply sheath 3, hits the flanged portion 44 and flows out along substantially the entire outer surface of the glass plate 32.

As shown in FIG. 9, the ultrasound vibration f generated on the vibration surface which is the inner surface (back side) of the glass plate 32 to which the piezoelectric transducer 37 is attached propagates inside the glass plate 32 in a substantially vertical direction to the vibration surface. This ultrasound vibration f reaches the diffraction grating 40, is converted by the diffraction grating 40 to the surface acoustic wave Φ that propagates on the outer surface of the glass plate 32 and propagates toward the center side (the photographing optical axis O side condensed by the image pickup optical system of the image pickup module 34) of the glass plate 32 as shown in FIG. 10 and toward the outer circumferential portion on the opposite side of the center side across the diffraction grating 40 within the outer surface of the glass plate 32 rectilinearly in the horizontal direction as the surface acoustic wave Φ. The direction of a grating vector that defines the traveling direction (propagation direction) of the surface acoustic wave Φ generated by the diffraction grating 40 is defined as the direction of periodicity of the diffraction grating 40. Here, since the diffraction grating 40 has a configuration in which linear grooves are arranged in parallel, the surface acoustic wave Φ propagates in two traveling directions opposite to each other across the diffraction grating 40 in directions orthogonal to the grooves.

If the glass plate 32 is not provided with the diffraction grating 40, since directivity of the ultrasound vibration f is high, the ultrasound vibration f repeats reflections between the plane of the piezoelectric transducer 37 and the outer surface of the glass plate 32 facing the plane of the piezoelectric transducer 37, and vibration therefore propagates well between these parts facing each other, but the ultrasound vibration f does not propagate well in a region distant from the piezoelectric transducer 37 of the glass plate 32.

On the contrary, when the diffraction grating 40 is provided on the outer surface of the glass plate 32 as in the case of the present embodiment, the ultrasound vibration f which proceeds straight forward from the piezoelectric transducer 37 is converted to the linear surface acoustic wave Φ by the diffraction grating 40 propagating toward the center direction (direction in which the photographing optical axis O passes) of the region of the observation field of view Lf (shown by a two-dot dashed line in FIG. 10) of the image pickup module 34 in the glass plate 32.

In other words, as shown in FIG. 10, the surface acoustic wave Φ is radiated in a direction perpendicular to the array direction of the grooves of the diffraction grating 40. The surface acoustic wave Φ propagating in the center direction of the glass plate 32 reaches and passes through the region of the observation field of view Lf on the outer surface of the glass plate 32. The surface acoustic wave Φ then pushes out and removes the dirt 101 such as blood stuck to the region of the observation field of view Lf in the propagation direction simultaneously with the supply of the cleaning water. The surface acoustic wave Φ propagates by concentrating its vibration on the surface of the glass plate 32, and can thereby efficiently transmit vibration to the dirt 101 stuck to the outer surface of the glass plate 32 and remove the dirt.

That is, when the ultrasound vibration f generated impinges on the diffraction grating 40, the ultrasound vibration f is converted to the surface acoustic wave Φ propagating in the photographing optical axis O direction. The diffraction grating 40 allows even the high frequency ultrasound vibration f with high directivity to efficiently propagate as the surface acoustic wave Φ in the center direction of the glass plate 32 (direction in which the photographing optical axis O passes), causing the dirt 101 stuck to the outer surface to mix with the cleaning water, partially atomizing the dirt or partially washing the dirt away together with the cleaning water and thereby making it possible to efficiently and reliably remove the dirt 101 over substantially the entire surface of the region of the observation field of view Lf in the glass plate 32.

When the surface acoustic wave Φ reaches the outer circumferential portion (surface corners) which is the outside part forming the contours of the outer surface of the glass plate 32, the wave mode is converted mainly from the surface acoustic wave Φ to the bulk wave Φb by the stepped portion 32a and deflected (converted) as bulk wave Φb scattering into the glass plate 32. As a result, the intensity of the surface acoustic wave Φ reflected by the outer circumferential portion of the glass plate 32, which propagates on the outer surface of the glass plate 32 from the outer circumferential portion to the region of the observation field of view LF, decreases.

If the stepped portion 32a is not formed in the outer peripheral corner of the glass plate 32, which converts the wave mode from the surface acoustic wave Φ to the bulk wave Φb to suppress reflections as the surface acoustic wave, the surface acoustic wave Φ which propagates from the diffraction grating 40 to the region of the observation field of view Lf and the surface acoustic wave Φ reflected by the outer circumference of the glass plate 32 or by the inner surface of the outer circumference directed to the region of the observation field of view Lf having relatively different (approximately different opposite) directions simultaneously coexist on the outer surface of the glass plate 32. This results in a case where the surface acoustic waves Φ whose traveling directions are opposite to each other act on the dirt 101 stuck to the outer surface of the glass plate 32 simultaneously, which may significantly reduce the performance of removing the dirt 101.

By contrast, the present embodiment forms, in the outer circumferential portion on the outer surface side of the glass plate 32, the stepped portion 32a that converts the surface acoustic wave Φ that propagates within the outer surface of the glass plate 32 to the bulk wave Φb that scatters into the glass plate 32, which makes the surface acoustic wave Φ propagating from the diffraction grating 40 toward the center direction of the region of the observation field of view Lf the principal wave on the outer surface (surface) of the glass plate 32 in the observation field of view, causing the surface acoustic wave Φ to act on the dirt 101 in one direction and making it possible to efficiently remove the dirt.

Furthermore, the endoscope 2 of the present embodiment also has an advantage of eliminating the necessity of providing extra components such as an absorption member to absorb the surface acoustic wave Φ.

As described so far, the endoscope system 1 of the present embodiment allows the ultrasound vibration f of the piezoelectric transducer 37 to efficiently propagate so as to travel in the center direction of the glass plate 32, in other words, the center direction of the region of the observation field of view Lf of the image pickup module 34 and makes it possible to efficiently remove the dirt 101 on the outer surface of the glass plate 32 facing the image pickup module 34 of the endoscope 2, and in the region of the observation field of view Lf in particular.

Second Embodiment

Figure 11A:
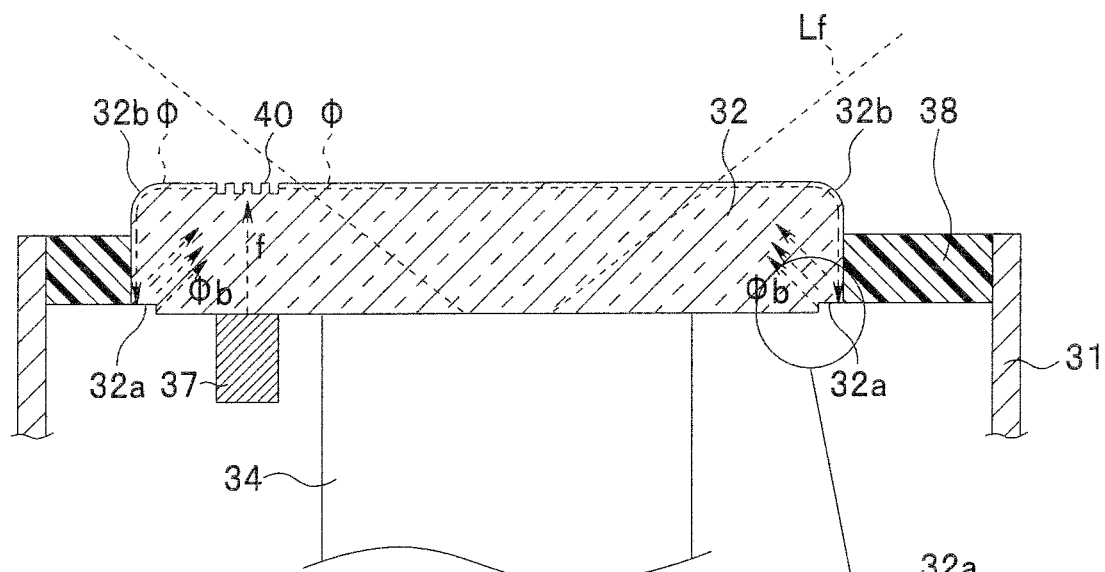
FIG. 11A is related to a second embodiment of the present invention and is a cross-sectional view illustrating a configuration of the distal end portion of a rigid endoscope.
Figure 11B:
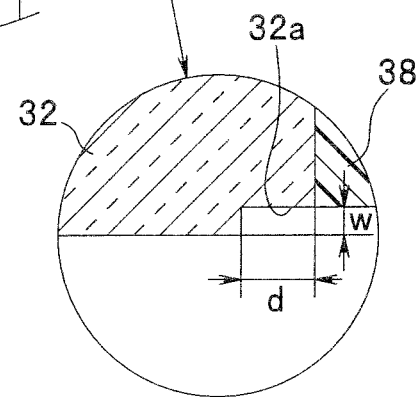
FIG. 11B is an enlarged cross-sectional view of a circled portion in FIG. 11A according to the second embodiment of the present invention.
Figure 12:
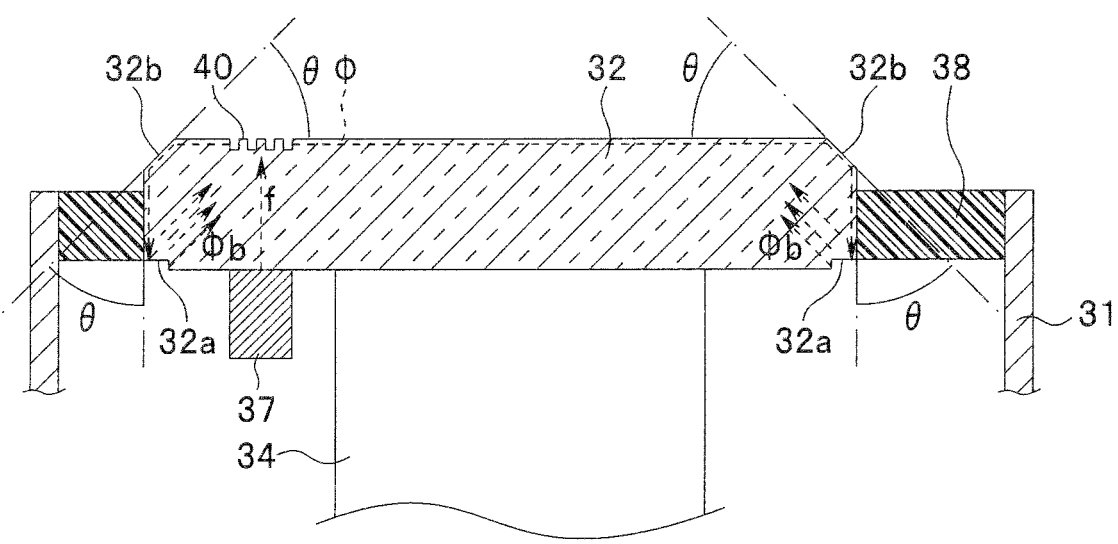
FIG. 12 is a cross-sectional view illustrating a configuration of the distal end portion of a rigid endoscope according to a modification example of the second embodiment of the present invention.

Next, a second embodiment of the endoscope system 1 of the present invention will be described in detail below based on FIGS. 11A and 11B, and FIG. 12. FIGS. 11A and 11B, and FIG. 12 are related to the second embodiment of the present invention, FIG. 11A is a cross-sectional view illustrating a configuration of the distal end portion of a rigid endoscope, FIG. 11B is an enlarged cross-sectional view of the circled portion in FIG. 11A and FIG. 12 is a cross-sectional view illustrating a configuration of the distal end portion of a rigid endoscope according to a modification example.

In the descriptions of the present embodiment, the components described in the first embodiment will be assigned the same reference numerals and descriptions of the configuration and operation thereof will be omitted. Moreover, the configuration of the present embodiment described below is naturally applicable to the endoscope 2 of the first embodiment as well.

As shown in FIGS. 11A and 11B, according to the present embodiment, a curved surface that functions as a deflection portion 32b is formed in the corner where the surface which is the outer surface of the glass plate 32 and a side peripheral surface (side surface) which is the outer circumferential face intersect each other, and a stepped portion 32a that functions as a mode conversion section is provided in the corner where the back side surface which is the inner surface of the glass plate 32 and a side peripheral surface (side surface) which is the outer circumferential face intersect each other.

In the present embodiment as well, the width w of the step is defined by the propagation direction of the surface acoustic wave Φ, that is, the propagation direction of the surface acoustic wave Φ within the side of the glass plate 32. The depth of the step is defined by the direction perpendicular to the propagation direction of the surface acoustic wave Φ, that is, the direction perpendicular to the side surface of the glass plate 32. Furthermore, the deflection portion 32b provided in the outer circumferential portion of the outer surface may be made up of a plane that crosses the outer surface (surface) and the side peripheral surface (side surface) at an angle of approximately 45 degrees ($\theta \approx 45°$ in the figure) as shown in FIG. 12.

Ultrasound vibration f that proceeds straight forward from the piezoelectric transducer 37 is converted to a surface acoustic wave Φ by the diffraction grating 40 and radiated in a direction parallel to the grating vector of the diffraction grating 40. Upon reaching the deflection portion 32b provided in the outer circumferential portion of the outer surface of the glass plate 32, the surface acoustic wave Φ radiated from the diffraction grating 40 propagates from the surface to the side surface along the curved surface and then reaches the stepped portion 32a provided in the outer circumferential portion of the inner surface (back corner).

The surface acoustic wave Φ that propagates (travels) to the outer circumferential portion of the inner surface (back corner) of the glass plate 32 by means of the stepped portion 32a is converted in wave mode from mainly the surface acoustic wave Φ to a bulk wave (rob and deflected (converted) as the bulk wave Φb that scatters into the glass plate 32. As a result, the component of the wave which is reflected as the surface acoustic wave Φ in the outer circumferential portion (side surface portion) of the glass plate 32 and returned from the outer circumferential portion in the direction of the region of the observation field of view Lf decreases, and it is possible to efficiently remove the dirt 101 on the outer surface (surface) of the glass plate 32 facing the image pickup module 34 of the endoscope 2, in the region of the observation field of view Lf in particular.

In addition to the aforementioned effect of the first embodiment, the present embodiment reduces the difference in level on the outer surface (surface) of the glass plate 32 as much as possible, and thereby has an effect of improving cleaning/sterilization performance.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope apparatus comprising:
a transparent member provided at a distal end of an insertion portion of an endoscope, opposed to an image pickup optical system;
a transducer attached to an inner surface of the transparent member;
a diffraction grating provided on an outer surface of the transparent member to convert ultrasound vibration from the transducer to a surface acoustic wave that propagates on the outer surface of the transparent member; and
a conversion section that converts the surface acoustic wave to a bulk wave that scatters into the transparent member in an outer peripheral corner of the transparent member.

2. The endoscope apparatus according to claim 1, wherein the conversion section is a stepped structure in which with respect to a wavelength $\lambda$ of the surface acoustic wave, a width of $0.25\lambda$ to $0.8\lambda$ is set in a direction parallel to a propagation direction of the surface acoustic wave and a depth of $0.7\lambda$ to $1.2\lambda$ is set in a direction orthogonal to the propagation direction of the surface acoustic wave.

3. The endoscope apparatus according to claim 2, wherein the conversion section is provided in corners where the outer surface and a side surface of the transparent member intersect each other.

4. The endoscope apparatus according to claim 2, wherein the conversion section is provided in corners where the inner surface and a side surface of the transparent member intersect each other, and
a deflection portion that causes the propagated surface acoustic wave to deflect toward a plane different from the outer surface is provided in corners where the outer surface and the side surface of the transparent member intersect each other.

5. The endoscope apparatus according to claim 4, wherein the deflection portion is made up of a curved surface or a plane that intersects the outer surface and the side surface at an angle of approximately 45 degrees.

6. The endoscope apparatus according to claim 1, wherein the conversion section is provided in corners where the outer surface and a side surface of the transparent member intersect each other.

7. The endoscope apparatus according to claim 1, wherein the conversion section is provided in corners where the inner surface and a side surface of the transparent member intersect each other, and
a deflection portion that causes the propagated surface acoustic wave to deflect toward a plane different from the outer surface is provided in corners where the outer surface and the side surface of the transparent member intersect each other.

8. The endoscope apparatus according to claim 7, wherein the deflection portion is made up of a curved surface or a plane that intersects the outer surface and the side surface at an angle of approximately 45 degrees.

* * * * *